United States Patent
Anderson

(10) Patent No.: US 9,572,638 B1
(45) Date of Patent: Feb. 21, 2017

(54) IMPRESSION COPING SPACER AND METHOD OF DENTAL CASTING

(71) Applicant: Lloyd T. Anderson, Willmar, MN (US)

(72) Inventor: Lloyd T. Anderson, Willmar, MN (US)

( * ) Notice: Subject to any disclaimer, the term of this patent is extended or adjusted under 35 U.S.C. 154(b) by 131 days.

(21) Appl. No.: 14/293,567

(22) Filed: Jun. 2, 2014

(51) Int. Cl.
*A61C 8/00* (2006.01)
*A61C 9/00* (2006.01)

(52) U.S. Cl.
CPC ........... *A61C 8/0001* (2013.01); *A61C 9/0006* (2013.01)

(58) Field of Classification Search
CPC ............ A61C 5/10; A61C 5/125; A61C 8/00; A61C 8/0001; A61C 8/0018–8/0025; A61C 8/005; A61C 8/0054; A61C 8/0056–8/0063; A61C 9/00; A61C 9/0006; A61C 9/0093; A61C 11/08; A61C 13/0027; A61C 13/20
USPC ....... 433/34, 37, 39, 40–42, 45, 47, 48, 167, 433/172–176, 202.1, 212.1, 213, 214
See application file for complete search history.

(56) References Cited

U.S. PATENT DOCUMENTS

| | | | |
|---|---|---|---|
| 1,478,019 A | 12/1923 | Brown | |
| 2,196,258 A | 4/1940 | Erdle | |
| 2,206,502 A | 7/1940 | Heiligman | |
| 2,579,960 A | 12/1951 | Pita et al. | |
| 2,755,552 A | 7/1956 | Brandau | |
| 3,328,879 A | 7/1967 | Bax | |
| 3,335,495 A | 8/1967 | Wichner | |
| 3,461,560 A | 8/1969 | Hana | |
| 3,660,899 A | 5/1972 | Linkow | |
| 3,716,918 A | 2/1973 | Tole et al. | |
| 3,748,739 A | 7/1973 | Thibert | |
| 3,838,187 A | 9/1974 | Thomas | |
| 3,871,804 A | 3/1975 | Cooper | |
| 3,882,601 A * | 5/1975 | Jahn | 433/214 |
| 3,955,280 A | 5/1976 | Sneer | |
| 3,971,133 A | 7/1976 | Mushabac | |
| 4,122,606 A | 10/1978 | Roman | |

(Continued)

FOREIGN PATENT DOCUMENTS

DE    WO 2008145687 A1 * 12/2008 ........... A61C 8/0001

OTHER PUBLICATIONS

Translation of WO2008145687a1.*

*Primary Examiner* — Nicholas Lucchesi
*Assistant Examiner* — Matthew Saunders
(74) *Attorney, Agent, or Firm* — Skinner and Associates; Joel D. Skinner

(57) ABSTRACT

A prosthodontic casting is formed from an implant osseointegrated within a bone and an impression coping coupled with the implant. An impression coping spacer circumscribes a supra-mucosal portion of the impression coping. A relatively high viscosity casting composition is applied to openings in a tray, and then the tray and relatively high viscosity casting composition placed to encompass the supra-mucosal portion of the impression coping and the impression coping spacer. The relatively high viscosity casting composition is at least partially cured, and then the impression coping spacer is extracted from the casting composition. This creates a void about the impression coping. An impression casting composition is then injected into the void and cured to form the prosthodontic casting. The now substantially cured combination casting composition and impression casting composition is removed from the implant, and subsequently used to guide the formation of a dental prosthesis.

12 Claims, 4 Drawing Sheets

(56) References Cited

U.S. PATENT DOCUMENTS

| | | | | |
|---|---|---|---|---|
| 4,172,867 | A | 10/1979 | Devault | |
| 4,204,321 | A | 5/1980 | Scott | |
| 4,242,089 | A | 12/1980 | Sasaki | |
| 4,253,835 | A | 3/1981 | Ware | |
| 4,622,011 | A | 11/1986 | Malek | |
| 4,690,643 | A | 9/1987 | Rousseau | |
| 4,744,753 | A | 5/1988 | Ross | |
| 4,744,756 | A | 5/1988 | Ross | |
| 4,892,478 | A | 1/1990 | Tateosian et al. | |
| 4,995,811 | A | 2/1991 | Cecconi | |
| 5,106,300 | A * | 4/1992 | Voitik | 433/173 |
| 5,211,561 | A | 5/1993 | Graub | |
| 5,221,204 | A | 6/1993 | Kruger et al. | |
| 5,221,205 | A | 6/1993 | Kuch | |
| 5,234,339 | A | 8/1993 | Grigereit | |
| 5,234,341 | A | 8/1993 | Johansen | |
| 5,234,343 | A | 8/1993 | Shoher et al. | |
| 5,238,405 | A | 8/1993 | Marlin | |
| 5,242,303 | A | 9/1993 | De Buck | |
| 5,259,759 | A * | 11/1993 | Jorneus et al. | 433/173 |
| 5,350,297 | A * | 9/1994 | Cohen | 433/76 |
| 5,439,380 | A | 8/1995 | Marlin | |
| 5,516,288 | A | 5/1996 | Sichler et al. | |
| 5,613,852 | A | 3/1997 | Bavitz | |
| 5,678,993 | A | 10/1997 | Jeffer et al. | |
| 5,695,335 | A | 12/1997 | Haas et al. | |
| 5,722,832 | A * | 3/1998 | White | A61C 9/00 433/214 |
| 5,807,100 | A | 9/1998 | Thornton | |
| 5,846,079 | A * | 12/1998 | Knode | 433/213 |
| 5,944,525 | A | 8/1999 | Ura | |
| 5,944,526 | A | 8/1999 | Liu | |
| 5,947,732 | A | 9/1999 | Beaty et al. | |
| 6,083,005 | A | 7/2000 | Taub | |
| 6,120,293 | A | 9/2000 | Lazzara et al. | |
| 6,247,926 | B1 * | 6/2001 | Thornton | A61C 9/00 433/214 |
| 6,315,562 | B1 | 11/2001 | Kumar | |
| 6,332,777 | B1 | 12/2001 | Sutter | |
| 6,379,148 | B1 | 4/2002 | Chen | |
| 6,382,977 | B1 | 5/2002 | Kumar | |
| 6,565,357 | B1 * | 5/2003 | Lazzara et al. | 433/173 |
| 6,769,913 | B2 | 8/2004 | Hurson | |
| 6,786,722 | B2 | 9/2004 | Craig et al. | |
| 6,814,577 | B2 | 11/2004 | Blacklock | |
| 6,824,386 | B2 | 11/2004 | Halldin et al. | |
| 6,881,360 | B2 | 4/2005 | Stange et al. | |
| 6,905,336 | B2 | 6/2005 | Summers | |
| 7,566,412 | B2 | 7/2009 | Sun et al. | |
| 7,632,095 | B2 * | 12/2009 | Ostman et al. | 433/172 |
| 7,905,726 | B2 | 3/2011 | Stumpel | |
| 8,011,925 | B2 | 9/2011 | Powell et al. | |
| 8,135,492 | B2 | 3/2012 | Yau et al. | |
| 8,454,363 | B2 | 6/2013 | Worthington | |
| 8,469,710 | B2 | 6/2013 | Bondar | |
| 8,572,848 | B2 | 11/2013 | Hayashi et al. | |
| 8,628,327 | B1 * | 1/2014 | Blaisdell et al. | 433/213 |
| 2002/0106610 | A1 * | 8/2002 | Hurson | 433/173 |
| 2003/0082498 | A1 * | 5/2003 | Halldin et al. | 433/173 |
| 2003/0082499 | A1 * | 5/2003 | Halldin et al. | 433/173 |
| 2004/0241610 | A1 * | 12/2004 | Hurson | 433/173 |
| 2006/0121416 | A1 * | 6/2006 | Engman | 433/173 |
| 2010/0248180 | A1 * | 9/2010 | Bondar | 433/141 |
| 2012/0270179 | A1 * | 10/2012 | Holmstrom et al. | 433/173 |
| 2013/0101964 | A1 * | 4/2013 | Fudim | 433/214 |
| 2013/0130202 | A1 * | 5/2013 | Vuillemot | A61C 13/34 433/213 |
| 2014/0170597 | A1 * | 6/2014 | Honig | 433/173 |

* cited by examiner

Fig. 7
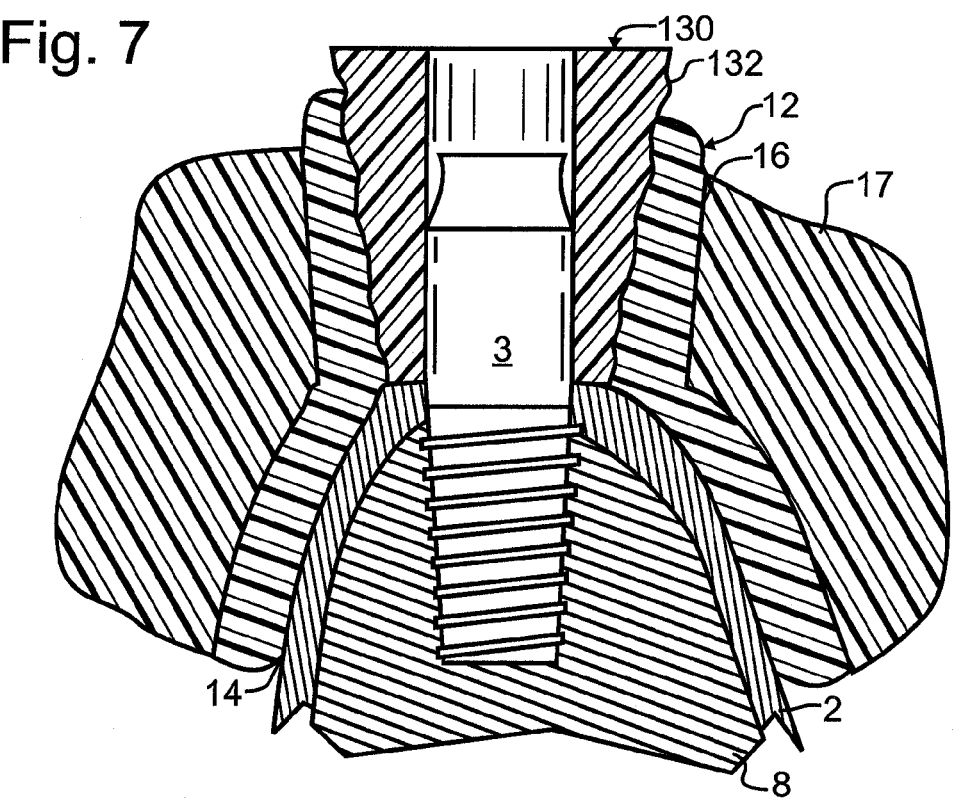
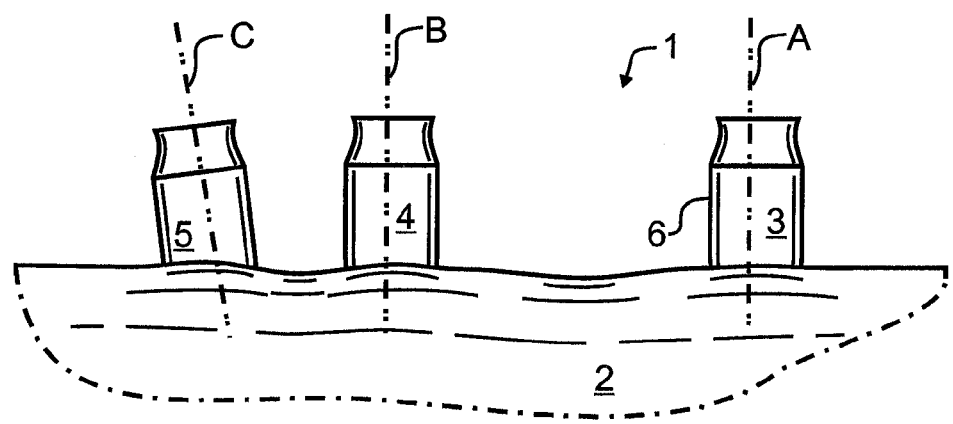
Fig. 8 (PRIOR ART)

IMPRESSION COPING SPACER AND METHOD OF DENTAL CASTING

BACKGROUND OF THE INVENTION

1. Field of the Invention

This invention pertains generally to dentistry, and more particularly to apparatus and methods used in prosthodontics. In one manifestation, the present invention facilitates the formation of an impression of one or more impression copings or final abutments attached to dental implants.

2. Description of the Related Art

Primary or deciduous teeth form in humans very early, typically while still in the embryonic stage. As a person develops and ages, these deciduous teeth are normally lost and replaced by permanent teeth. While most teeth will typically last for decades with reasonable care, injury and disease will eventually take a toll on these permanent teeth, leading to loss thereof. This loss of permanent teeth makes chewing more difficult or in some cases impossible. In addition, the missing teeth may adversely affect a person's speech and cosmetic appearance, which in turn can adversely affect their confidence and attitude.

In some cases, a dental prosthesis may be attached directly to surrounding teeth. However, this is not always possible or practical. Where a surrounding-tooth dental prosthesis is impractical, a dental implant may be installed into a bone such as the mandibular or maxillary bones. This implant can serve as an anchor that substitutes for and thereby replaces the need for surrounding teeth. While there are a wide variety of known dental implants, such as those illustrated in at least some of the patents incorporated by reference herein below, they will typically have a mounting substructure that is anchored within the bone, and which typically terminates below, adjacent to, or slightly above the gum line. Coupled with this mounting substructure is an abutment or mounting stud. The mounting stud rises above the gum line, and provides a mounting to which a dental prosthesis may then be affixed. Prior art FIG. 8 depicts this in simplified form through one exemplary configuration and from an elevational view showing the oral cavity 1 and mandible covered with soft mucosal tissue 2 commonly referred to as the gums or gingiva. Rising from the gums 2 are three impression copings 3, 4, and 5. The actual geometry of these impression copings 3, 4, and 5 and associated implants is not critical to the present invention, and as noted may vary by manufacturer. Typical impression copings might, for exemplary purposes, have a first column or body 6 rising from the gums 2. Again, the geometry of the column 6 will vary from manufacturer to manufacturer. Columns 6 will typically each define a longitudinal axis illustrated as axes A, B, and C in FIG. 8 that each rise from or extend generally normal to the mandible or maxilla, much as a typical tooth would. Desirably, axes A, B, and C will all be parallel, but there may be some axial deviation, such as axis C in FIG. 6, which is angularly offset from axes A and B, and which deviates from normal to or perpendicular to the mandible. In addition to angular misalignment, there is also the potential for deviation in the spacing between adjacent implants.

Once the implants have been inserted into the maxilla or mandible and allowed to osseointegrate therewith, a casting is necessary to form a dental prosthesis. This casting must accurately reflect the actual locations and axial orientations of mounting studs that will be coupled to the implants, so that a dental prosthesis fabricated using the casting will properly engage and fit with the implants and mounting studs. When implants are used, there are no periodontal ligaments to absorb inaccuracies. Even very minor inaccuracies between prosthesis, mounting studs and implants can lead to bone resoprtion, loosening or breaking of prosthetic parts, or even failures in the osseointegration of the implant into bone. Consequently, it is very important to properly reproduce the patient's oral cavity 1 adjacent to the implants and any adjacent teeth. A laboratory will then be able to produce a proper dental prosthesis.

To obtain the casting, a temporary extension referred to as an impression coping is typically fastened to the implant. Next, a two-part resin-based casting composition may be applied that cures in only a few minutes. Once cured, the copings may be unscrewed or otherwise detached from the implants, and the casting removed. The casting may then be used to guide the formation of the dental prosthesis.

Undesirably, the fluid liquid resin binder used in the casting compositions is well-known to shrink both unevenly and unpredictably upon curing and hardening. In addition, the potential exists for the formation of voids in the casting which do not accurately reflect the geometry of the oral cavity 1.

To reduce unpredictable shrinkage and distortion, various fillers are known and regularly added to the resin. These fillers resist shrinkage and distortion when used at sufficiently elevated concentrations in combination with the fluid liquid resin binder. Unfortunately, they also increase the viscosity of the casting composition, changing the composition from a low viscosity fluid to a higher viscosity paste as the filler concentrations are increased. When the viscosity of the casting composition increases, it is less likely to pick up detail in the oral geometry, and more likely to retain undesirable voids. However, the high viscosity casting compositions also tend to be more durable and less likely to tear or fracture when being removed from the oral cavity. Heretofore, this has forced a dentist to choose between either low viscosity composition or high, and in the process sacrifice at least some desired features.

While FIG. 8 illustrates one exemplary configuration of impression copings, it will be understood that very different and diverse geometries may present, varying from patient to patient. Further, with more than one implant and impression coping, the need for accuracy increases. Unfortunately, the shrinkage and distortion may be additive. This means the potential exists for shrinkage adjacent one impression coping that is away from the second coping, while the shrinkage adjacent the second impression coping may also be away from the first coping. In such a case, the tolerances are effectively cut in half for a satisfactory dental prosthesis.

In view of the limitations of the prior art, several artisans have proposed different techniques for overcoming these limitations. U.S. Pat. No. 6,905,336 by Summers, entitled "Impression support system for dental implants", the teachings and contents which are incorporated herein by reference, illustrates a semi-rigid coping reinforcement system comprising a number of crossbraces. The crossbraces must be manually inserted and adjusted to accommodate different distances required for different patients. These crossbraces must also maintain sufficient rigidity to resist the shrinkage and distortion of the impression material. As may be appreciated, the adjustability and rigidity are once again conflicting desires, and the installation time and complexity is also undesirable. A similar reinforcing structure is illustrated in U.S. Pat. No. 3,748,739 by Thibert, entitled "Oral implant stabilizer and denture support", the teachings and contents which are incorporated herein by reference.

Another approach that has been proposed is an intra-oral scanning, such as described in U.S. Pat. No. 8,011,925 by Powell et al, entitled "Methods for manufacturing dental implant components", the teachings and contents which are incorporated herein by reference. These systems are very expensive, difficult to operate owing to the difficulty in distinguishing saliva and other debris from tissue, and do not afford any immediate tangible product that can be inspected and validated by the dentist. Consequently, a patient may be forced to wait not only for one lab production of the prosthesis, but one or more subsequent productions until the prosthesis is perfected. It is exactly this delay that the shrinkage and distortion of prior art casting materials undesirably causes. As a result, the intra-oral scanning equipment has not been widely accepted.

In U.S. Pat. No. 6,769,913 by Hurson, entitled "Impression cap", the teachings which are incorporated herein by reference, an impression cap is provided as a part of a kit used by a dentist. The impression cap is designed to preferably snap on to the exterior of a final abutment. The dentist then injects impression material into the cap, to fill the void between impression cap and final abutment. Next, a U-shaped impression tray filled with a second impression material is pressed over the impression cap and cured, embedding the impression cap and first material therein into the casting. While the apparatus and methods illustrated in the Hurson patent represent significant advancement over the prior art, the impression cap must be specifically designed for a particular abutment. In addition, since the impression cap surrounds the abutment and encloses it, such that the void is only accessible through a small top opening, the dentist cannot visually ascertain the fill, and instead must rely upon the impression material extruding from the impression cap as the indicator that the void has been filled. In the Hurson patent, the dentist also has little control over the thickness of the impression material from the top of the abutment to the top of the impression cap. While this thickness would preferably be consistent across the entire area filled by the impression material, to ensure flow the Hurson impression cap has a much thicker region of impression material directly above the abutment, thinning to the lower region of the abutment most adjacent to the mucosal tissue. While this variation is less than found in the prior art, such variation will tend to increase the unpredictability of shrinkage in the casting. In addition, the second impression material in the U-shaped tray will shrink and distort unpredictably, and will thereby alter the final casting geometry detrimentally.

Additional United States patents, the teachings and contents which are incorporated herein by reference, include: U.S. Pat. No. 1,478,019 by Brown, entitled "Dental impression guide"; U.S. Pat. No. 2,196,258 by Erdle, entitled "Method of molding ceramic articles"; U.S. Pat. No. 2,206,502 by Heiligman, entitled "Shaped material for casting dentures"; U.S. Pat. No. 2,579,960 by Pita et al, entitled "Method of making artificial dentures"; U.S. Pat. No. 2,755,552 by Brandau, entitled "Dental protheses, jaw-splints and jacket-crowns"; U.S. Pat. No. 3,328,879 by Bax, entitled "Means for resiliently mounting artificial teeth"; U.S. Pat. No. 3,335,495 by Wichner, entitled "Sectional preformed full dentures and method of assembling the same"; U.S. Pat. No. 3,461,560 by Hana, entitled "Method of forming a prosthetic dental appliance and an impression tray therefor"; U.S. Pat. No. 3,660,899 by Linkow, entitled "Bridge stabilizing system"; U.S. Pat. No. 3,716,918 by Tole et al, entitled "Denture coupling and method of forming coupling"; U.S. Pat. No. 3,838,187 by Thomas, entitled "Dental model construction method"; U.S. Pat. No. 3,871,804 by Cooper, entitled "Dental restoration jig"; U.S. Pat. No. 3,955,280 by Sneer, entitled "Dental implants"; U.S. Pat. No. 3,971,133 by Mushabac, entitled "Dental restoration"; U.S. Pat. No. 4,122,606 by Roman, entitled "Method and apparatus for mounting dental die models in dental stone"; U.S. Pat. No. 4,172,867 by Devault, entitled "Index pin and die spacer combination for dental model"; U.S. Pat. No. 4,204,321 by Scott, entitled "Dental post"; U.S. Pat. No. 4,242,089 by Sasaki, entitled "Dental prosthesis"; U.S. Pat. No. 4,253,835 by Ware, entitled "Post and sleeve arrangement"; U.S. Pat. No. 4,622,011 by Malek, entitled "Radicular post head comprising reversible retention and automatic positioning means"; U.S. Pat. No. 4,690,643 by Rousseau, entitled "Dental fastening device and method of use"; U.S. Pat. No. 4,744,753 by Ross, entitled "Methods for forming dental prosthesis"; U.S. Pat. No. 4,744,756 by Ross, entitled "Apparatus for forming dental prosthesis"; U.S. Pat. No. 4,892,478 by Tateosian et al, entitled "Method of preparing dental appliances"; U.S. Pat. No. 4,995,811 by Cecconi, entitled "Component part removable partial denture and method for designing and making same"; U.S. Pat. No. 5,211,561 by Graub, entitled "Coupling device for dental prothesis"; U.S. Pat. No. 5,221,204 by Kruger et al, entitled "Dental implant product and method of making"; U.S. Pat. No. 5,221,205 by Kuch, entitled "Bridge with lingual bolt locking attachment"; U.S. Pat. No. 5,234,339 by Grigereit, entitled "Implant supported prosthesis"; U.S. Pat. No. 5,234,341 by Johansen, entitled "Wearer-removable dental implant attachment"; U.S. Pat. No. 5,234,343 by Shoher et al, entitled "Moldable dental material and method"; U.S. Pat. No. 5,238,405 by Marlin, entitled "Implant collar and post system"; U.S. Pat. No. 5,242,303 by De Buck, entitled "Method for the realization of an implant prosthesis and parts hereby applied"; U.S. Pat. No. 5,259,759 by Jorneus et al, entitled "Temporary cylinder"; U.S. Pat. No. 5,439,380 by Marlin, entitled "Method of forming an abutment post"; U.S. Pat. No. 5,516,288 by Sichler et al, entitled "Device and method for attaching a member in replacement of part of a set of teeth"; U.S. Pat. No. 5,613,852 by Bavitz, entitled "Dental implant drill guide system"; U.S. Pat. No. 5,678,993 by Jeffer et al, entitled "Methods of lining dentures and denture voids and forming denture extensions"; U.S. Pat. No. 5,695,335 by Haas et al, entitled "Dental implant"; U.S. Pat. No. 5,807,100 by Thornton, entitled "Dental device having an improved deformable material and method for forming same"; U.S. Pat. No. 5,944,525 by Ura, entitled "Dental implant and method and apparatus for installing the same"; U.S. Pat. No. 5,944,526 by Liu, entitled "Method and apparatus for a dental implant system"; U.S. Pat. No. 5,947,732 by Beaty et al, entitled "Support post for use in dental implant system"; U.S. Pat. No. 6,083,005 by Taub, entitled "Method of use of natural latex emulsion"; U.S. Pat. No. 6,120,293 by Lazzara et al, entitled "Abutment for a temporary tooth"; U.S. Pat. No. 6,315,562 by Kumar, entitled "Implant carrier with gripping fingers"; U.S. Pat. No. 6,332,777 by Sutter, entitled "Device for forming a dental prosthesis"; U.S. Pat. No. 6,379,148 by Chen, entitled "Method of locating a dental implant"; U.S. Pat. No. 6,382,977 by Kumar, entitled "Snap-in impression coping"; U.S. Pat. No. 6,786,722 by Craig et al, entitled "Orthodontic modeling filler material and method"; U.S. Pat. No. 6,814,577 by Blacklock, entitled "Dental prosthesis abutment and waxing sleeve assembly"; U.S. Pat. No. 6,824,386 by Halldin et al, entitled "Components for improved impression making"; U.S. Pat. No. 6,881,360 by Stange et al, entitled "Process for producing a prosthesis and a prosthesis material"; U.S. Pat. No. 7,566,412 by Sun et al, entitled "Dental method and device"; U.S. Pat. No. 7,905,726 by Stumpel, entitled "Surgical guide for dental implant and methods therefor"; U.S. Pat. No. 8,135,492 by Yau et al, entitled "Method of making a surgical template used for a computer-guided dental implant surgery"; U.S. Pat. No. 8,454,363 by Worthington, entitled "Dental implant system"; U.S. Pat. No. 8,469,710 by Bondar, entitled "Dental implant system and method"; and U.S. Pat. No. 8,572,848 by Hayashi et al, entitled "Method for manufacturing dental implant". In addition to the aforementioned patents, Webster's New Universal Unabridged Dictionary, Second Edition copyright 1983, is incorporated herein by reference in entirety for the definitions of words and terms used herein.

SUMMARY OF THE INVENTION

In a first manifestation, the invention is a prosthodontic casting comprising an implant osseointegrated within a bone and an impression coping coupled with the implant. An impression coping spacer is adapted to operatively circumscribe a supra-mucosal portion of the impression coping. A first casting composition which may have a relatively high viscosity encompasses the supra-mucosal portion of the impression coping and the impression coping spacer and thereby defines an inner casting surface adjacent to a mucosal tissue. The impression coping spacer is adapted to be operatively extracted from the relatively high viscosity first casting composition and thereby form a void between the relatively high viscosity first casting composition and the supra-mucosal portion of the impression coping that is operative to receive a relatively low viscosity casting composition.

In a second manifestation, the invention is a method of dental casting. According to the method, an impression coping spacer is placed around an impression coping affixed to an implant. A casting composition that may have a relatively high viscosity is applied to a dental tray, and then the tray is placed adjacent to mucosal tissue surrounding and adjacent to the impression coping spacer. The impression coping spacer is removed from between the relatively high viscosity first casting composition and the impression coping to thereby create a void about the impression coping without adversely disrupting the relatively high viscosity casting composition. The relatively high viscosity casting composition is at least partially cured. The void about the impression coping is filled with a relatively low viscosity impression casting composition. The combination at least partially cured relatively high viscosity casting composition and relatively low viscosity impression casting composition is removed from the implant, and used to guide the formation of a dental prosthesis.

OBJECTS OF THE INVENTION

Exemplary embodiments of the present invention solve inadequacies of the prior art by providing an impression coping spacer between a relatively high viscosity casting composition and a supra-mucosal portion of an impression coping. The impression coping spacer is adapted to be operatively extracted from the relatively high viscosity casting composition and thereby form a void between the relatively high viscosity casting composition and the supra-mucosal portion of the impression coping. The void is then filled with a relatively low viscosity impression casting composition.

The present invention and the preferred and alternative embodiments have been developed with a number of objectives in mind. While not all of these objectives are found in every embodiment, these objectives nevertheless provide a sense of the general intent and the many possible benefits that are available from embodiments of the present invention.

A first object of the invention is to use a higher viscosity casting material having good durability and tear and fracture resistance for casting. A second object of the invention is to allow the primary casting material to at least partially polymerize or cure, with any associated dimensional changes, without altering critical locations in the casting. Another object of the present invention is to provide an improved process of forming a casting that requires relatively less time and precision to produce an extremely accurate and high quality impression. An additional object of the invention is to provide apparatus and methods that are either operable without alteration or readily adaptable to a wide variety of impression copings such as are available commercially.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which:

FIG. 7 illustrates an alternative embodiment impression coping spacer in combination with a simplified prior art impression coping and implant, and in further combination with a relatively high viscosity casting composition held within a tray similar to that illustrated in FIG. 2, from a sectional view taken along a vertical plane parallel to axis A in FIG. 8.

FIG. 8 illustrates a prior art and simplified arrangement of impression copings osseointegrated within a mandible, from an elevational view.

DESCRIPTION OF THE PREFERRED EMBODIMENT

Figure 1:
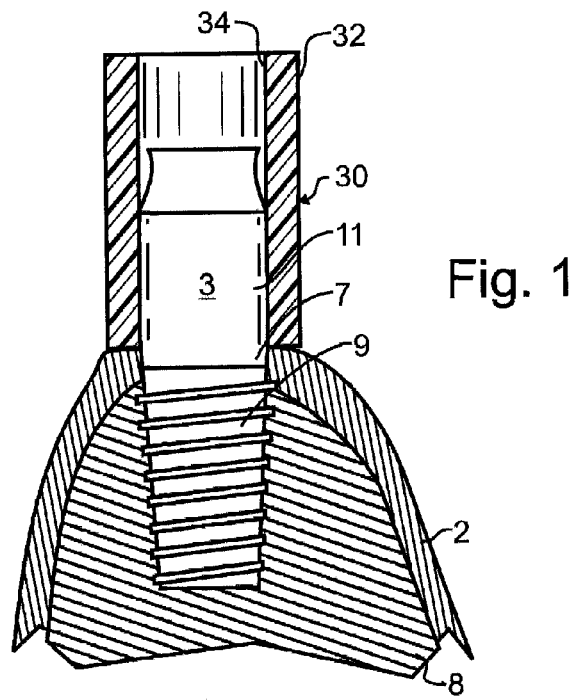
FIG. 1 illustrates a preferred impression coping spacer designed in accord with the teachings of the present invention in combination with a simplified prior art impression coping coupled with an implant osseointegrated within a mandible, from a sectional view taken along a vertical plane parallel to axis A in FIG. 8.
Figure 2:
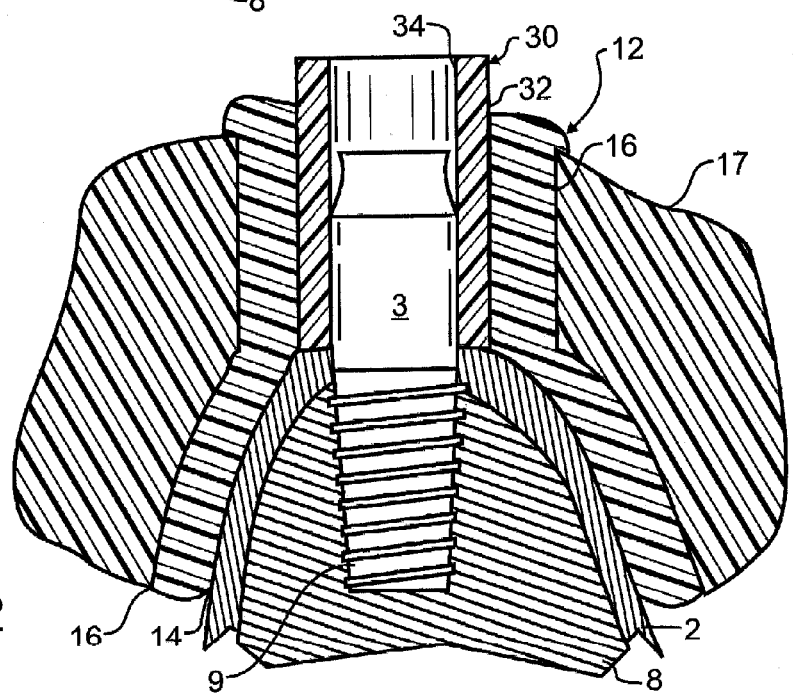
FIG. 2 illustrates the preferred impression coping spacer in combination with a simplified prior art impression coping and implant of FIG. 1, and in further combination with a relatively high viscosity casting composition held within a tray, from a sectional view taken along a vertical plane parallel to axis A in FIG. 8.

Manifested in the preferred embodiment, the present invention provides an impression coping spacer 30 adapted to circumscribe the supra-mucosal portion 11 of an impression coping 3. The impression coping mucosal portion 7, surrounded by soft mucosal tissue 2, affixes to an implant 9 osseointegrated within a bone such as the mandible 8 covered by gums 2 as illustrated in FIG. 1. While a mandible 8 is illustrated, it will be apparent to those skilled in the art that other suitable anchoring may be provided and is contemplated herein, including but not limited to a maxillary anchoring. Furthermore, the impression coping 3 and implant 9 have been greatly simplified in the illustration, and may comprise any of the known implants and impression copings including but not limited to those illustrated in the patents incorporated by reference herein above.

Impression coping spacer 30 in the preferred embodiment of FIG. 1 has a generally tubular or annular geometry, including an outer surface 32 and an inner surface 34. In the preferred embodiment of FIG. 1, impression coping spacer 30 is slightly resilient, and inner surface 34 defines an inside diameter that may be slightly less than, equal to, or only nominally greater than the outside diameter of impression coping 3. If of smaller inside diameter, this causes impression coping spacer 30 to stretch slightly when applied to impression coping 3, to ensure a reasonably leak-tight connection sufficient to prevent the ingress of casting composition 12 there between. Nevertheless, the essential requirement is that there is no consequential seepage of casting composition reasonably possible between impression coping spacer 30 and impression coping 3.

The particular geometry of impression coping spacer 30 is not limited to tubular construction with circular or annular cross-section, and so may include other geometries such as extruded hexagonal or other polygonal cross-sectional geometries having open or hollow cores. The particular geometries available will depend upon factors including but not limited to the resilience of the material used to fabricate impression coping spacer 30; the viscosity of casting composition 12; and the exterior geometry of the exposed portion of impression coping 3. Since casting composition 12 is preferably relatively more viscous, the fitting between impression coping spacer 30 and impression coping 3 in the preferred embodiment can be quite loose. In further contemplated embodiments, impression coping spacer 30 may comprise additional features or components known in the hardware arts to improve the seal with impression coping 3, such as for exemplary purposes but not solely limited thereto: one or more internal rings or features of smaller inside diameter than the primary inside diameter; additional layers or materials between inner surface 34 and impression coping and implant 3 that seal or adhere the two together; and any other suitable known features and components.

Once preferred impression coping spacer 30 has been placed around impression coping 3, as illustrated in FIG. 1, a relatively high viscosity casting composition 12 will be applied to one or more openings formed in a tray 17. Tray 17 may, for exemplary purposes only and not solely limiting thereto, resemble that shown in Craig et al or Hurson incorporated by reference herein above. In an alternative embodiment contemplated herein, tray 17 may be fabricated by a dentist specifically for use with a particular patient.

The one or more openings in tray 17 will preferably be formed to correspond to the locations of the implants and impression copings, and will also preferably be formed to have an inside geometry that corresponds to or resembles the geometry of the patient's adjacent oral cavity 1 including gums 2. As noted herein above though not essential to the invention, with sufficient filler material, casting composition 12 will not flow freely away from the site of application. This allows casting composition 12 to be manually applied to tray 17 just prior to application of casting composition 12 and tray 17 to the one or more impression copings. In the preferred embodiment, a relatively high viscosity casting composition 12 is quickly and efficiently applied to tray 17, and tray 17 with casting composition 12 then manually applied to surrounding mucosal tissue 2 and adjacent to and encompassing impression coping spacer 30. An inner casting surface 14 preferably follows the contours and geometry of gums 2, and the thickness between the inner casting surface 14 and outer casting surface 16 is preferably relatively constant.

While a variety of known and commercially available casting materials may be used, and the invention is not limited to one or another, in the preferred embodiment a two-part composition that is mixed within an applicator nozzle is preferred. Commercially available two-part compositions are known and commercially available that have sufficient strength and hardness within only a few minutes to permit the dentist to proceed with the casting process.

Figure 3:
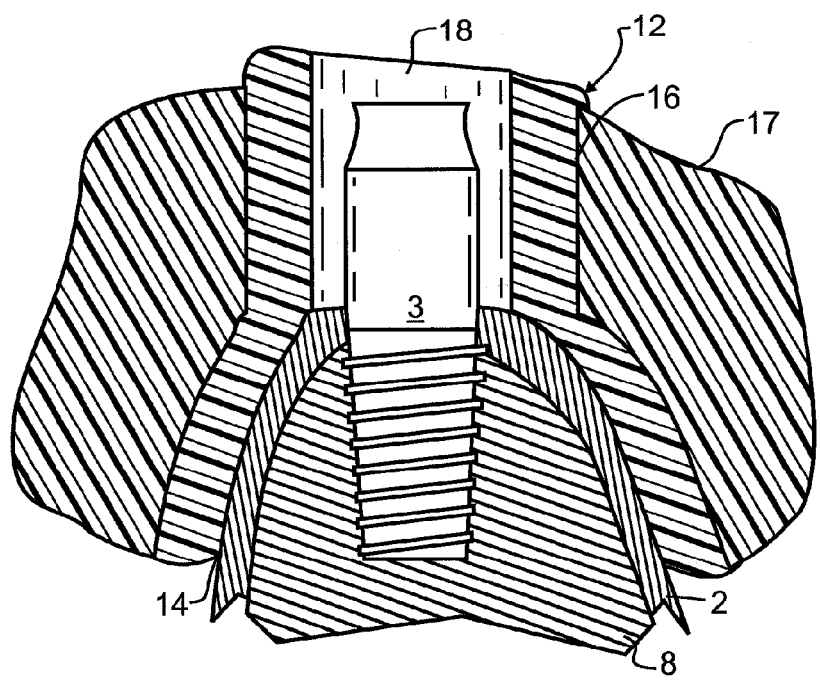
FIG. 3 illustrates the preferred simplified prior art impression coping and implant in combination with a relatively high viscosity casting composition held within a tray of FIG. 2, but with the impression coping spacer removed therefrom to leave a void about the coping, from a sectional view taken along a vertical plane parallel to axis A in FIG. 8.

As illustrated in FIG. 3, impression coping spacer 30 is removed from between casting composition 12 and impression coping and implant 3 to leave a void 18 about the impression coping. This may be done manually, and may employ any convenient tool or implement such as pliers. If outer surface 32 of impression coping spacer 30 is relatively linear in the longitudinal direction, meaning there are no obstructions to linear movement, and as long as there is no other chemical or mechanical bonding there between, then impression coping spacer 30 may be easily slid out from within casting composition 12 without adversely disrupting casting composition 12. This means that it is somewhat less critical how long a dentist waits to remove impression coping spacer 30, so long as the material selected for impression coping spacer 30 is relatively inert with respect to casting composition 12 and the outer surface 32 is mechanically free of consequential obstructions, protrusions or indentations. A generally smooth and consistent tubular geometry is therefore preferred for impression coping spacer 30, and a hollow cylindrical geometry most preferred. Most extrusions have sufficiently consistent exterior geometry in the longitudinal direction to define preferred geometries.

In an alternative embodiment illustrated in FIG. 7, an impression coping spacer 130 may be provided having a conical outer surface 132. The angular slope of the cone may be relatively small. Nevertheless, and for exemplary and non-limiting purpose only, this deviation allows outer surface 132 to be textured rather than smooth. A textured surface for the primary and relatively more viscous casting composition 12 may provide a stronger mechanical bond to the secondary and relatively less viscous casting composition 20.

Since impression coping spacers 30, 130 are designed to be separated from casting composition 12, a material selected for impression coping spacers 30, 130 is therefore preferred that is chemically inert with respect to casting composition 12. Contemplated herein for exemplary purposes but not solely limiting the invention thereto are such compositions as polyethylene; polypropylene; vinyl; polyvinyl chloride; polyvinylidene chloride; tetrafluoroethylene; other fluorinated or chlorinated hydrocarbons; cross-linked compositions such as various synthetic and natural rubbers; and other similar or suitable compositions.

As may be apparent from FIG. 3, once impression coping spacer 30 is removed, there is a relatively small void 18 that is preferably of substantially consistent thickness between casting composition 12 and impression coping 3. The size of void 18 is determined by the size of impression coping spacer 30. Casting composition 12 may, if so desired, then be allowed to further cure or polymerize. As long as the wall thickness of impression coping spacer 30 is sufficient, any associated dimensional changes or twisting will only alter the dimensions of void 18, without consequentially impacting the dimension of the final casting.

Figure 4:
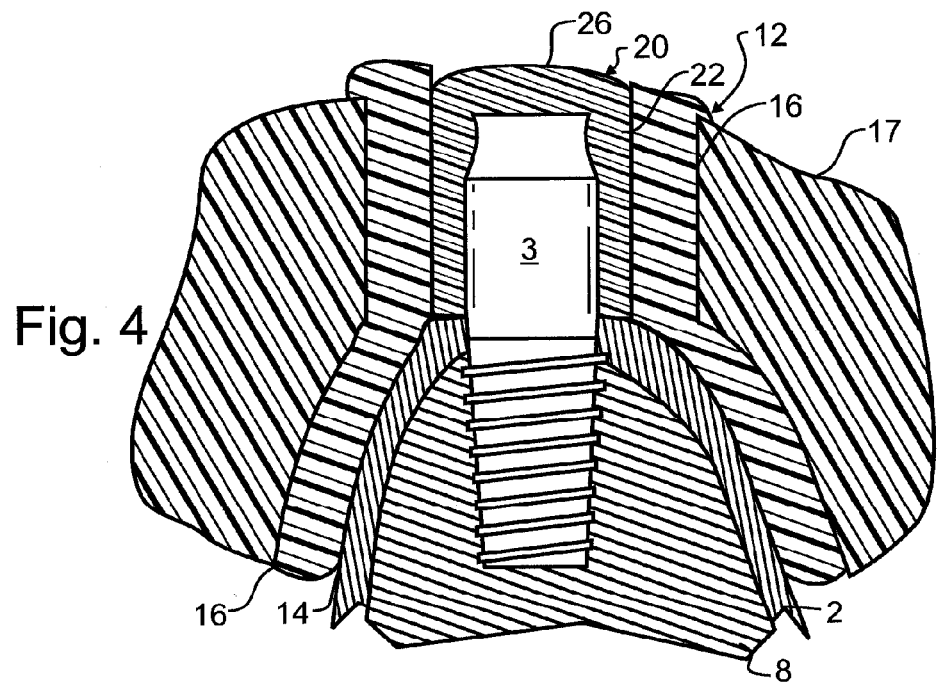
FIG. 4 illustrates the preferred simplified prior art impression coping and implant in combination with a relatively high viscosity casting composition held within a tray of FIG. 3, with the impression coping spacer void about the coping filled with a second casting composition, from a sectional view taken along a vertical plane parallel to axis A in FIG. 8.

As illustrated in FIG. 4, once impression coping spacer 30 has been removed and sufficient curing has occurred in casting composition 12, then void 18 about impression coping 3 may be filled with a relatively lower viscosity impression casting composition 20. The particular time required to allow casting composition 12 to cure before applying impression casting composition 20 will depend upon several variables, including the cure times of casting compositions 12 and 20; the level of precision desired; and the rate of deformation of the particular casting compositions. In other words, if nearly all of the deformation in casting composition 12 occurs in the first few minutes after nozzle-mixing during application, then there may be no delay required. However, if substantial deformation continues to occur within casting composition 12 for twenty minutes, then the dentist should allow twenty minutes between the application of casting composition 12 and impression casting composition 20. Likewise, even if casting composition 12 requires twenty minutes, if impression casting composition 20 is a slower curing material that requires more than twenty minutes to cure, then impression casting composition 20 may be applied essentially immediately. As should be apparent, this time between applying casting composition 12 and impression casting composition 20 will be a characteristic of the particular casting compositions selected. Once impression casting composition 20 has been applied, it will preferably form a tubular body 22 about impression coping and implant 3. Impression casting composition 20 may also form a crown 26 above void 18. While not essential to the present invention, it is preferable that impression casting composition have a substantially constant wall thickness throughout, which helps to avoid differential shrinkage or distortion during curing.

Figure 5:
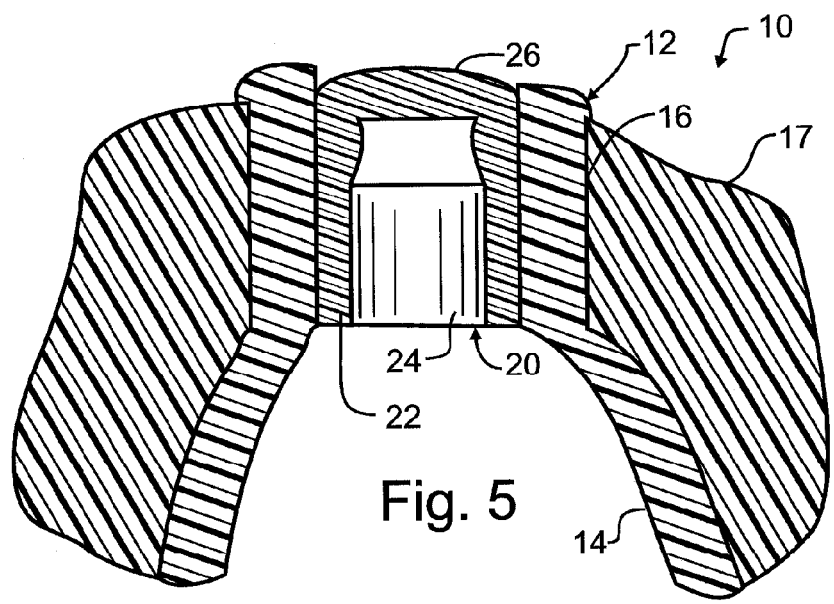
FIG. 5 illustrates the preferred combination relatively high viscosity casting and second casting of FIG. 4, removed from the mandible and optionally removed from the impression coping, from a sectional view taken along a vertical plane parallel to axis A in FIG. 8.

In the final step illustrated in FIG. 5, the preferred combination relatively high viscosity casting 12 and relatively low viscosity impression casting 20 may be removed from the mandible, maxilla or other body part. FIG. 5 illustrates impression casting composition 20 being completely separated from impression coping 3 and implant 9, revealing a hollow region 24 within tubular body 22, but this is for illustrative purposes and not a requirement of the present invention. In many cases, impression coping 3 will be separated from implant 9, and impression coping 3 may then remain with finished prosthodontic casting 10. Furthermore, and depending upon the geometry of the particular impression coping 3 selected, impression coping 3 may also pass through crown 26.

Figure 6:
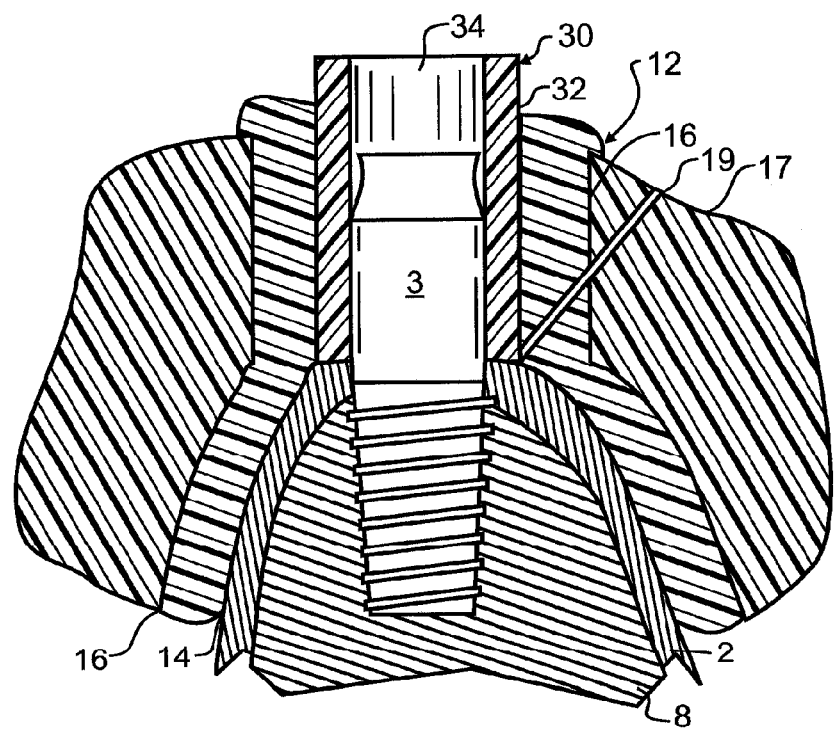
FIG. 6 illustrates the preferred embodiment impression coping spacer in combination with a simplified prior art impression coping and implant, and in further combination with a relatively high viscosity casting composition held within a tray similar to that illustrated in FIG. 2, and in further combination with an alternative embodiment injection port from a sectional view taken along a vertical plane parallel to axis A in FIG. 8.

In an alternative embodiment illustrated in FIG. 6, and generally mirroring that illustrated in FIG. 4, an additional injection port 19 may optionally be provided. Injection port 19 may pass solely through either tray 17 or casting composition 12, but as illustrated in the embodiment of FIG. 6, injection port 19 passes through both. Injection port 19 will preferably extend from the base of impression coping spacer 30 most nearly adjacent to the mucosal tissue or gums 2 outward and towards the opening of oral cavity 1. This allows a dentist to inject impression casting composition 20 directly in, potentially using impression casting composition 20 to drive impression coping spacer 30 out from casting composition 12. It will be understood that the diameter of injection port 19 will be sufficient to permit a syringe or equivalent tool to be inserted therein. Where the diameter is sufficient, the syringe may pass entirely through injection port 19. This allows a dentist to fill the syringe tip entirely with impression casting composition 20 prior to insertion into injection port 19, to eliminate the introduction of air therein. As long as the diameter of injection port 19 is sufficiently larger than the syringe tip to allow air to escape, but sufficiently small enough to prevent impression casting composition 20 from escaping up injection port 19 in any disruptive quantity, then no air will be introduced during the filling of void 18.

As may be appreciated, the present invention is not limited to a particular impression coping, and may be used with a wide variety of commercially available copings. The accuracy afforded will be present in most cases entirely independent of the particular copings used. This is particularly beneficial, since the circumstances or nature of some patients mandates different impression copings than might be used more generally with other patients.

If so desired, the accuracy of the preferred embodiment allows a finished prosthodontic casting to be scanned and a prosthodontic appliance machined using semi- or fully automated CAD/CAM equipment, thereby reducing manual labor. Further, the accuracy afforded by the present invention also increases the likelihood of long term success with the prosthodontic appliance, while also reducing the frequency of re-manufacturing or re-machining appliances.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

I claim:

1. A prosthodontic casting system for preparing a casting of an one or more impression copings and surrounding oral features of a patient, comprising:
    a dental implant adapted to be osseointegrated within a patient's bone;
    an impression coping having a mucosal portion adjacent a first end adapted to operatively couple with said dental implant and having a supra-mucosal portion distal to said mucosal portion;
    a transient impression coping spacer adapted to initially operatively circumscribe said supra-mucosal portion of said impression coping, wherein said impression coping spacer further comprises a conical geometry including a distally outwardly tapered outer surface, and a cylindrical inner surface adapted to releasibly contact said impression coping;

a first casting composition encompassing said supra-mucosal portion of said impression coping and said impression coping spacer and defining an inner casting surface of the oral features of a patient adjacent to and spaced from said supra-mucosal portion of said impression coping;

said impression coping spacer being adapted to be operatively extracted from said first casting composition and thereby form a void between said first casting composition and said supra-mucosal portion of said impression coping, said distally outwardly tapered surface adapted to releasibly contact said first casting composition, and an impression casting composition adapted to be disposed in said void after said impression coping spacer is extracted, and configured to establish a substantially consistent thickness between said first casting composition and said supra-mucosal portion of said impression coping, said impression casting composition being operatively coupled with said first casting composition to yield the cast of at least one impression coping and the oral features of the patient adjacent to the impression coping.

2. The prosthodontic casting system of claim 1, wherein said impression coping spacer is constructed of a resilient, stretchable material and further comprises a resilient inner surface defining an inside diameter that is slightly less than or equal to an outside diameter of said impression coping, wherein said impression coping spacer is adapted to operatively stretch slightly when applied to said impression coping to thereby operatively ensure a connection sufficient to seal and prevent ingress of said first casting composition between the impression coping spacer and the impression coping.

3. The prosthodontic casting system of claim 1, wherein the outer surface of said impression coping spacer is chemically and mechanically unbound from said first casting composition to permit extraction of the impression coping spacer from the first casting composition whereby said void may be formed.

4. The prosthodontic casting system of claim 1, wherein said impression coping spacer outer conical surface is textured, whereby the first casting composition is stronger mechanically bonded to the impression casting composition.

5. The prosthodontic casting system of claim 4, wherein said impression coping spacer further comprises materials substantially chemically inert with respect to said first casting composition and said impression casting composition.

6. The prosthodontic casting system of claim 1, further comprising a prosthodontic casting tray adapted to contain said first casting composition.

7. The prosthodontic casting system of claim 1, wherein said impression casting composition, prior to curing, has a lower viscosity than that of said first casting composition.

8. The prosthodontic casting system of claim 1, further comprising an injection port passing through said first casting composition, said injection port extending from the outer environment through the first casting composition adjacent to the coupling of the impression coping to the dental implant, the injection port adapted to permit introduction of the impression casting composition at adjacent to the coupling of the impression coping to the dental implant to facilitate extraction of the impression coping spacer from said first casting composition.

9. The prosthodontic casting system of claim 1, wherein:
A. said impression coping spacer outer conical surface is textured, whereby the first casting composition is stronger mechanically bonded to the impression casting composition, and
B. further comprising an injection port passing through said first casting composition, said injection port extending from the outer environment through the first casting composition adjacent to the coupling of the impression coping to the dental implant, the injection port adapted to permit introduction of the impression casting composition at adjacent to the coupling of the impression coping to the dental implant to facilitate extraction of the impression coping spacer from said first casting composition.

10. A method for preparing a prosthodontic cast at least one
impression coping coupled to a dental implant, and surrounding oral features of a patient,
comprising:
coupling an impression coping spacer on the supra-mucosal portion of the at least one impression coping, the impression coping spacer including an outer conical geometry with a distally outwardly tapered outer surface and a cylindrical inner surface adapted to releasably contact said impression coping;
placing a first casting composition encompassing the supra-mucosal portion of the impression coping and the impression coping spacer and defining an inner casting surface of the oral features of a patient adjacent to and spaced from the supra-mucosal portion of the impression coping;
extracting the impression coping spacer from the first casting composition and thereby forming a void between the first casting composition and the supra-mucosal portion of the impression coping, the distally outwardly tapered surface of the impression coping spacer releasing from contact with the first casting composition, and
placing an impression casting composition in the void after the impression coping spacer is extracted, the impression casting composition establishing a substantially consistent thickness between the first casting composition and the supra-mucosal portion of the impression coping, the impression casting composition being operatively coupled with the first casting composition to yield a cast of the at least one impression coping and the oral features of the patient adjacent to the at least one impression coping.

11. The method of claim 10, wherein the impression coping spacer outer conical surface is textured, whereby the first casting composition is stronger mechanically bonded to the impression casting composition.

12. The method of claim 10, further comprising an injection port passing through the first casting composition, said injection port extending from the outer environment through the first casting composition adjacent to the coupling of the impression coping to the dental implant, and wherein the step of extracting the impression coping spacer and the step of placing the impression casting composition are accomplished substantially simultaneously by injecting the impression casting composition into the injection port, the impression coping spacer being extracted by the force of the impression casting compound.

\* \* \* \* \*